(12) United States Patent
Rößler

(10) Patent No.: US 8,116,856 B2
(45) Date of Patent: Feb. 14, 2012

(54) ARRANGEMENT FOR RECORDING ECG SIGNALS

(75) Inventor: Jürgen Rößler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 235 days.

(21) Appl. No.: 11/986,858

(22) Filed: Nov. 27, 2007

(65) Prior Publication Data
US 2008/0125667 A1    May 29, 2008

(30) Foreign Application Priority Data
Nov. 28, 2006  (DE) .......................... 10 2006 056 156

(51) Int. Cl.
*A61B 5/04* (2006.01)
(52) U.S. Cl. ........................ 600/509; 600/393
(58) Field of Classification Search .................. 600/372, 600/373, 509, 382, 390, 391, 392, 393; 607/9, 607/142, 147
See application file for complete search history.

(56) References Cited

U.S. PATENT DOCUMENTS

| | | | | |
|---|---|---|---|---|
| 5,217,010 A | * | 6/1993 | Tsitlik et al. | 607/9 |
| 5,341,806 A | * | 8/1994 | Gadsby et al. | 600/393 |
| 6,070,097 A | | 5/2000 | Kreger et al. | |
| 6,201,981 B1 | * | 3/2001 | Yarita | 600/372 |
| 6,259,939 B1 | * | 7/2001 | Rogel | 600/390 |
| 6,415,169 B1 | * | 7/2002 | Kornrumpf et al. | 600/382 |
| 7,197,357 B2 | * | 3/2007 | Istvan et al. | 600/509 |
| 7,844,316 B1 | * | 11/2010 | Botero | 600/386 |
| 2004/0210149 A1 | * | 10/2004 | Wenger | 600/509 |
| 2004/0225210 A1 | | 11/2004 | Brosovich et al. | |
| 2005/0102015 A1 | * | 5/2005 | Lau et al. | 607/129 |
| 2006/0178574 A1 | * | 8/2006 | Fischer et al. | 600/372 |

FOREIGN PATENT DOCUMENTS
CH        426 968        6/1967
DE    10 2005 004 859 A1    8/2006
* cited by examiner

*Primary Examiner* — Brian T Gedeon

(57) ABSTRACT

The invention relates to an arrangement for recording ECG signals. The arrangement has at least three electrodes, which can be connected or are connected to an amplification unit via lines, with at least two lines having no or essentially only a minimal distance from one another at least over one part of their length and being embodied as a component of a cable comprising more than two lines.

13 Claims, 3 Drawing Sheets

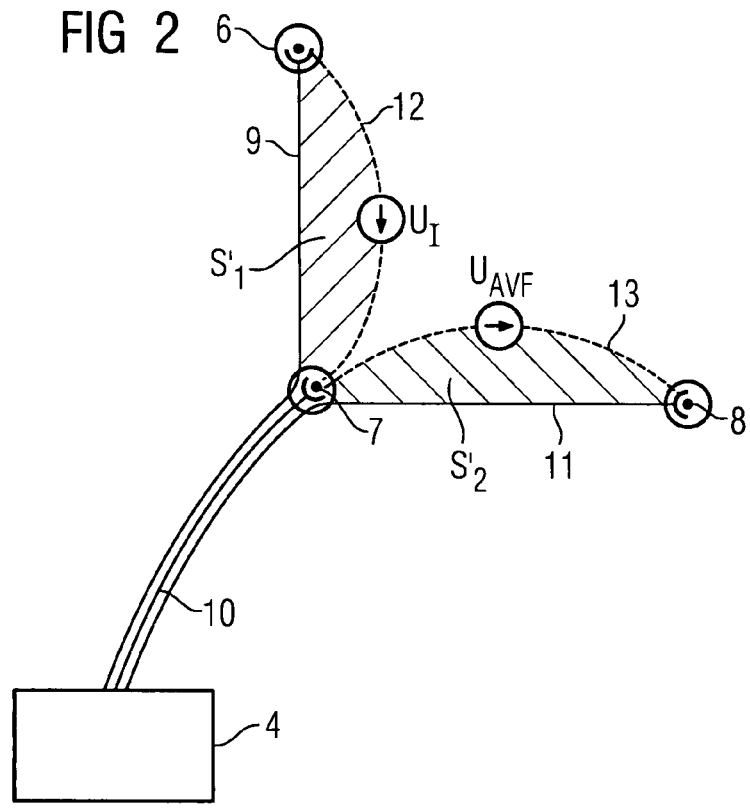
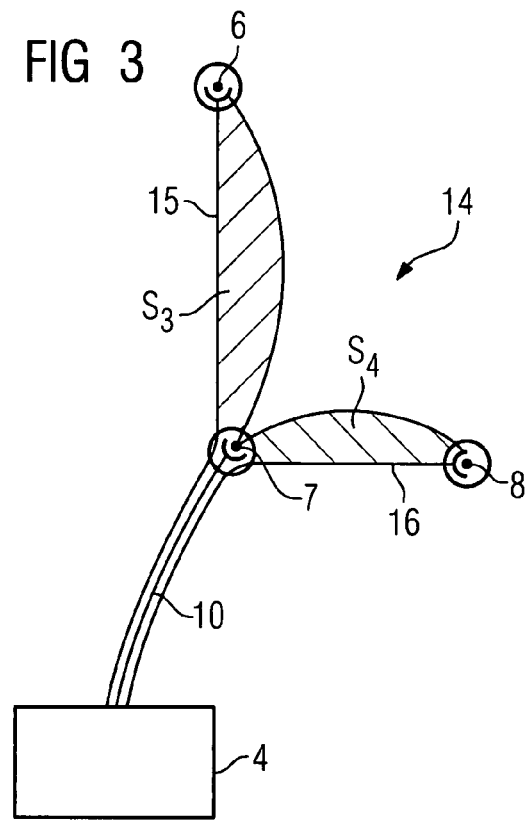

ARRANGEMENT FOR RECORDING ECG SIGNALS

CROSS REFERENCE TO RELATED APPLICATIONS

This application claims priority of German application No. 10 2006 056 156.2 filed Nov. 28, 2006, which is incorporated by reference herein in its entirety.

FIELD OF THE INVENTION

The invention relates to an arrangement for recording ECG signals, having at least three electrodes, which can be connected or are connected to an amplification unit by way of lines.

BACKGROUND OF THE INVENTION

Magnetic resonance tomography (MR) requires ECG signals of the patient to be recorded in order to synchronize the triggering of MR measurement sequences to the heartbeat of the patient. The information relating to the current heart phase can likewise be obtained by the ECG signal recorded during an MR examination. If the ECG signals and the triggering and/or activation of the measurement sequence are not synchronized, there is a risk that the MR images contain movement artifacts.

In practice however, recording ECG signals is associated with difficulties, since the electrical and magnetic fields which take effect during the MR sequences are coupled into the ECG electronics system in a considerably interfering manner, thereby negatively affecting the reliable determination of the heart phase. Aside from these unwanted couplings into the ECG electronic system, the so-called magneto-hydrodynamic effect occurs in the case of higher magnetic flow densities, which result in an excessive rise in the T-wave of the heartbeat. In the field of electrocardiography, the different phases of the heart cycle are identified with letters, by the sequence P-Q-R-S-T for instance. In this process, the R-wave shows the greatest deflection, and is the reference point of the triggering and must consequently be determined in a reliable fashion.

A method for the ECG triggering of a measurement sequence of a magnetic resonance device is known from U.S. Pat. No. 6,070,097, but the ECG signals of a patient are recorded there by way of a single channel.

WO 99/04688 proposed the recording of two ECG channels, from which a vector representation in a coordinate system is derived. It should be possible to infer the R-wave of the heart cycle from this representation. It is however doubtful whether this method is sufficiently reliable, since this vector projection is dependent on many influences, for instance it changes if the patient holds his breath.

US 2004/0225210 A1 discloses an electrode arrangement, in which a number of lines are guided in parallel to each other.

DE 10 2005 004 859 A1 describes an ECG electrode arrangement for MR applications, in which each electrode line is assigned a correction line, which is insulated therefrom, in order to avoid unwanted induction voltages.

A typical conventional arrangement for recording ECG signals is shown schematically in FIG. 1. The arrangement includes three electrodes 1, which are each connected to a line 3 by way of clasps 2, the individual lines 3 are guided to an amplification unit 4, in which they are amplified for further processing purposes. The electrodes 1 are positioned on the thorax of a patient, it being possible for the cables 3 to be laid in any fashion. It is also possible to use more than three electrodes.

The recording of voltages U1 and U2 shown in FIG. 1 is carried out by way of two loops, which are each formed by two lines 3 and a path 5 in the body, shown with a dashed line. The ECG signal to be derived can be regarded as the voltage source $U_1$ or $U_{AVF}$.

A voltage for each loop can be measured on the amplification unit 4, said voltage being the sum of the derived ECG signal and an induced voltage part. The induced voltage part effects the interfering couplings into the ECG signal and can be calculated according to the law of induction. The surfaces $S_1$ and $S_2$ in this process correspond in each instance to the loop, which is formed by two lines and the path lying therebetween in the body of the patient. The larger this surface, the greater also the unwanted induced voltage.

If the ECG signals are recorded in order to trigger the measurement of a magnetic resonance device, the problem arises that the changing magnetic fields cause interferences to be coupled into the ECG signal. In the prior art, it has been proposed to filter out or suppress these interferences by means of a complex signal processing method. This procedure nevertheless requires a significant outlay for the signal processing.

SUMMARY OF THE INVENTION

The object underlying the invention is thus to specify an arrangement for recording ECG signals, in which the influence of interfering magnetic fields is reduced and does not require a complex signal processing procedure.

With an arrangement of the type mentioned in the introduction, in order to achieve this object, provision is made in accordance with the invention for at least two lines to have no or essentially only a minimal distance from one another at least over part of their length and for the at least two lines to be embodied as a component of a cable comprising more than two lines.

The knowledge underlying the invention is that the interfering couplings into the ECG signal can be reduced, by minimizing the surface formed between two lines. The interfering couplings are thus directly minimized at the site of their creation.

Within the scope of the invention, provision is made for the at least two lines to run parallel to each another and for said lines to be embodied as a component of a cable comprising a plurality of lines. In this case, the distance between the lines is constant and very minimal and/or absolutely no appreciable distance is present, so that the surface spanned between the lines is also insignificantly small, thereby resulting in practically no interfering voltages being induced.

The section of the lines, in which the at least two lines have no or only a minimal distance from each another, is preferably located between the amplification unit and a branching point. In the further course from the branching point to the electrodes, the lines run at a distance from one another. The surface spanned in this case is however essentially smaller by comparison with conventional arrangements, in which the lines run from the amplification unit to the electrodes independently and separately from one another.

Provision can also be made for the branching point to be located on or in the vicinity of an electrode. By way of example, two lines can be routed up to the branching point, at which an electrode is present, and one of these lines can be routed past the branching point. With other embodiments of the invention, provision can be made for the sections of the at least two lines to essentially have the same length between the branching point and the electrodes. Alternatively, they can however also have a different length.

The number of lines used with the arrangement according to the invention is at least three, but naturally a larger number of lines can be used, with an electrode being located at each end of a line.

BRIEF DESCRIPTION OF THE DRAWINGS

Further advantages and details of the invention are described on the basis of exemplary embodiments with reference to the figures. The figures are schematic illustrations in which:

FIG. 2 shows a first exemplary embodiment of the invention;

FIG. 3 shows a second exemplary embodiment of the invention, and

DETAILED DESCRIPTION OF THE INVENTION

FIG. 2 shows a first exemplary embodiment of the invention. The arrangement for recording ECG signals includes three electrodes 6, 7 8, which are each connected to the amplification unit 4 by way of a line 9, 10, 11. In the exemplary embodiment illustrated, the lines 9 and 11 have the same length, the line 10, which connects the electrode 7 to the amplification unit 4, is on the other hand shorter. As FIG. 2 shows, the lines 9, 10, 11 between the amplification unit 4 and a branching point, which coincides with the site of the electrode 7, are arranged in parallel to each another, so that they have no or only a very minimal distance from each another. The lines 9, 11 run separately from one another from the branching point to the end points of the lines 9, 11, which are formed by the electrodes 6, 8.

FIG. 2 also shows schematic paths 12, 13, which are to illustrate the conductive sections in the body of a patient. The ECG signals $U_1$ and $U_{AVF}$ to be derived are shown as a voltage source in FIG. 2. It is clear that the surfaces $S_1$, and $S_2$, enclosed by the paths 12, 13 and the corresponding lines 9, 11 are essentially smaller by comparison with the surfaces of FIG. 1, so that the interfering induced voltages are likewise considerably reduced.

Figure 1:
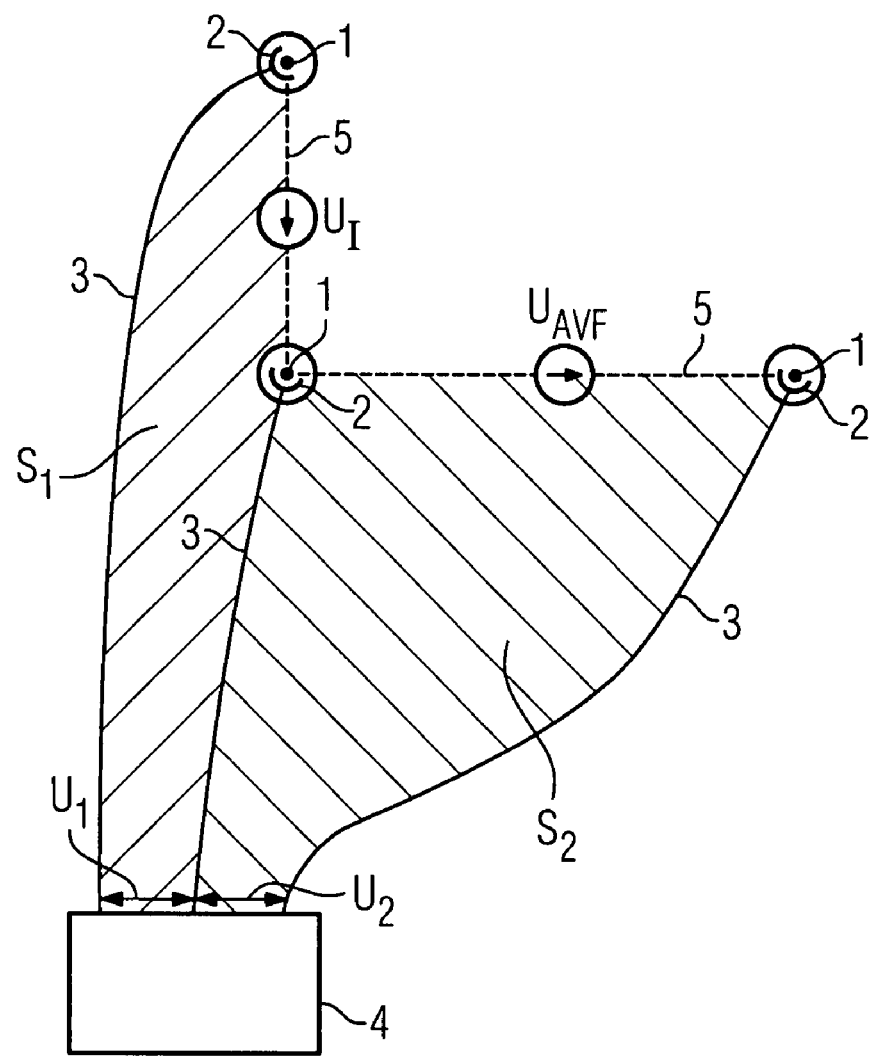
FIG. 1 shows a conventional arrangement for recording ECG signals.

FIG. 3 shows a second exemplary embodiment of the invention, with the same reference characters as in FIG. 2 being used for corresponding components. In conformance with the exemplary embodiment in FIG. 2, the arrangement 14 according to the invention includes electrodes 6, 7, 8, which are connected to an amplification unit 4 by way of lines. The electrode 6 is connected to the amplification unit by way of a line 15, the electrode 7 is connected to the amplification unit by way of a line 16, the electrode 7 is connected to the amplification unit 4 by way of a line 10. The lines 10, 15, 16 have a common section, over which they are routed in parallel, said section being embodied as a cable with three internal lines. In contrast to the exemplary embodiment shown in FIG. 2, the sections of the lines 15, 16 have different lengths between the branching point and the electrodes 6, 8, so that differently sized surfaces $S_3$, $S_4$ result, which are formed in each instance by the lines 15, 16 and the corresponding path in the body of the patient. However, these surfaces, upon which the size of the induced voltage depends, are small by comparison with those of the conventional arrangement, which is shown in FIG. 1.

Figure 4:
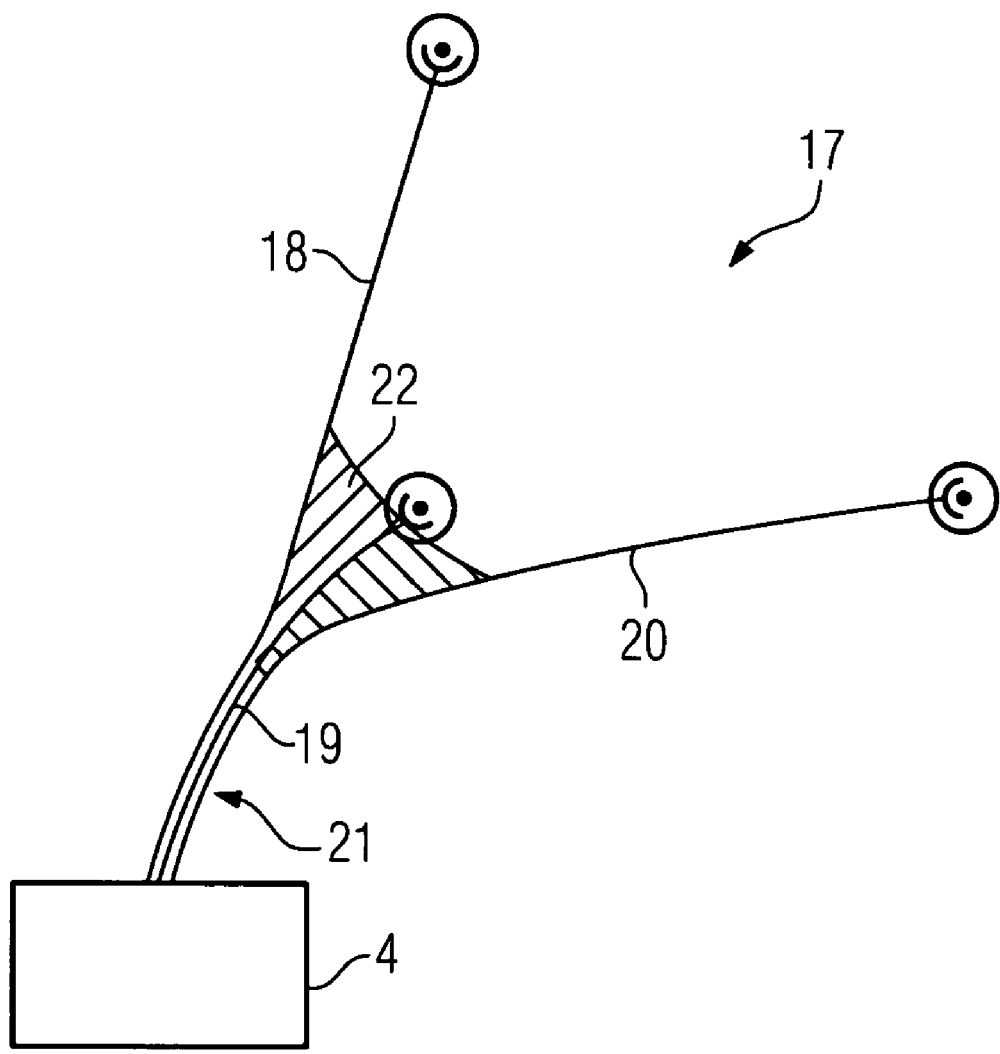
FIG. 4 shows a third exemplary embodiment of the invention.

FIG. 4 shows a third exemplary embodiment of the invention. The arrangement 17 for recording ECG signals includes three electrodes 1, which are connected to the amplification unit 4 by way of lines 18, 19, 20. The lines 18, 19, 20 are however only routed in parallel to each another in the section 21 which directly borders the amplification unit 4. The lines 18, 19, 20 subsequently branch out. In this branched region, an elastic membrane 22 is formed between the lines 18 and 19 as well as 19 and 20, it being possible to produce said elastic membrane from an elastomer or a rubber material for instance. The corresponding sections of the lines 18, 19, 20 are connected elastically to one another by means of the membrane 22, thereby preventing these sections from becoming separated from one another. On the other hand, it is easily possible to position the electrodes 1 on the body of a patient in an almost arbitrary manner. The membrane 22 then exerts a reset force on the corresponding sections of the lines 18, 19, 20, which causes the surfaces of the voltage loop to be reduced, thereby likewise reducing the unwanted inductive interferences.

The invention is not restricted to the exemplary embodiments illustrated, in particular arrangements for recording ECG signals are also conceivable, in which the differently described variants are combined or in which a larger number of electrodes or lines is present.

The invention claimed is:

1. A device for minimizing an interfering induced voltage when recording an ECG signal of an object, comprising:
    an amplification unit;
    a plurality of electrodes that record the ECG signal of the object and that are each individually configured to be placed on an object;
    a plurality of lines that each individually connect to an individual electrode of the electrodes to the amplification unit configured to be flexible to allow for independent and separate placement of each individual electrode on the object;
    a cable that comprises part of length of at least two lines of the plurality of lines and remaining part of length of the at least two lines extending from the cable; and
    an elastic membrane formed between the plurality of lines after the cable configured to exert a reset force on the plurality of lines when each electrode of the plurality of electrodes is individually, independently, and separately placed on the object to reduce inductive voltage;
    wherein the cable minimizes a distance between the at least two lines of the part of length in the cable; and
    wherein the cable maintains a minimum or no distance between the plurality of lines of the part of length of in the cable and the remaining part of length of the plurality of lines extending from the cable are configured to be placed independently and separately from one another.

2. The device as claimed in claim 1, wherein the at least two lines of the cable have a minimal distance between each other over a length of the at least two lines.

3. The device as claimed in claim 1, wherein the part of length of the at least two lines is a length from the amplification unit to a branching point.

4. The device as claimed in claim 3, wherein the branching point is located at or in a vicinity of one of the electrodes.

5. The device as claimed in claim 4, wherein the at least two lines have a same length between the branching point and the each individual electrode connected to each respective line.

6. The device as claimed in claim 4, wherein the at least two lines have a different length between the branching point and the each individual electrode connected to each respective line.

7. The device as claimed in claim 1, wherein the at least two lines are elastically connected to one another over a length of the at least two lines.

8. The device as claimed in claim 1, wherein the elastic membrane comprises an elastic belt and/or an elastic surface.

9. The device as claimed in claim 8, wherein the elastic belt and/or the elastic surface is detachable and/or removable.

10. A method minimizing an interfering induced voltage when recording an ECG signal of an object, comprising:
    independently, separately and individually placing at least two electrodes of a plurality of electrodes on an object;
    providing a cable comprising part of length of at least two lines of a plurality of lines and remaining part of length of the at least two lines extending from the cable, wherein the at least two lines are individually connected to the at least two electrodes, and wherein the cable minimizes a distance between the at least two lines of the plurality of lines of the part of length in the cable; and
    exerting a reset force between the at least two lines by elastically connecting the at least two lines after the cable to further minimize distance between the at least two lines when the electrodes are independently and separately placed from each other to reduce an interfering inductive voltage.

11. The method as claimed in claim 10, wherein the at least two lines have a minimal distance from each other over a length of the at least two lines.

12. The method as claimed in claim 10, wherein the length is from the amplification unit to a branching point.

13. The method as claimed in claim 10, wherein the branching point is located at or in a vicinity of one of the electrodes.

* * * * *